(12) United States Patent
Higashiyama

(10) Patent No.: US 12,345,442 B2
(45) Date of Patent: Jul. 1, 2025

(54) HUMIDIFIER

(71) Applicant: Murata Manufacturing Co., Ltd., Kyoto (JP)

(72) Inventor: Yuzo Higashiyama, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 610 days.

(21) Appl. No.: 17/659,193

(22) Filed: Apr. 14, 2022

(65) Prior Publication Data

US 2022/0235952 A1 Jul. 28, 2022

Related U.S. Application Data

(63) Continuation of application No. PCT/JP2020/033979, filed on Sep. 8, 2020.

(30) Foreign Application Priority Data

Oct. 17, 2019 (JP) .................................. 2019-190177

(51) Int. Cl.
*F24F 6/02* (2006.01)
*A61M 16/16* (2006.01)

(52) U.S. Cl.
CPC ............. *F24F 6/025* (2013.01); *A61M 16/16* (2013.01)

(58) Field of Classification Search
CPC ..... A61M 16/16; F24F 6/025; F24F 2006/008
USPC ...................................... 128/204.14; 261/72.1
See application file for complete search history.

(56) References Cited

U.S. PATENT DOCUMENTS

| | | | | |
|---|---|---|---|---|
| 5,354,515 A | * | 10/1994 | Ushimaru | F24F 6/12 261/81 |
| 5,564,415 A | * | 10/1996 | Dobson | A61M 16/109 220/795 |
| 2008/0072900 A1 | | 3/2008 | Kenyon et al. | |
| 2011/0155132 A1 | | 6/2011 | Virr | |

(Continued)

FOREIGN PATENT DOCUMENTS

| | | | |
|---|---|---|---|
| EP | 0001842 B1 | * | 7/1980 |
| JP | 2011-072830 A | | 4/2011 |

(Continued)

OTHER PUBLICATIONS

English Machine Translation of EP 0001842 B1 (Year: 1980).*
International Search Report for PCT/JP2020/033979 dated Nov. 24, 2020.

*Primary Examiner* — Charles S Bushey
(74) *Attorney, Agent, or Firm* — McDonald Hopkins LLC

(57) ABSTRACT

A humidifier includes a second housing. A water storage tank is in a housing space of the second housing. The tank is detachable through an attachment/detachment port of the second housing. A third introduction hole communicates an inside and an outside of the second housing with each other in the second housing. A first tank hole communicates an inside and an outside of the tank with each other in the tank. Between the second housing and the tank, a first seal member separates a first downstream side flow path leading to an inside of the tank through the third introduction hole and the first tank hole, from an external space of the second housing. The first seal member extends along an inner surface of the second housing to entirely surround the tank, when viewed from a top of the tank.

20 Claims, 10 Drawing Sheets

(56) References Cited

U.S. PATENT DOCUMENTS

| | | | |
|---|---|---|---|
| 2011/0215486 A1* | 9/2011 | Jury | F02M 3/12 |
| | | | 261/66 |
| 2014/0130802 A1* | 5/2014 | Virr | A61M 16/0875 |
| | | | 128/203.26 |
| 2017/0361053 A1 | 12/2017 | Dimatteo et al. | |
| 2018/0333556 A1 | 11/2018 | Ormrod et al. | |
| 2019/0143070 A1 | 5/2019 | Smith et al. | |

FOREIGN PATENT DOCUMENTS

| | | |
|---|---|---|
| JP | 2017-121502 A | 7/2017 |
| JP | 2017-537708 A | 12/2017 |

\* cited by examiner

PRIOR ART

HUMIDIFIER

CROSS REFERENCE TO RELATED APPLICATION

This is a continuation of International Application No. PCT/JP2020/033979 filed on Sep. 8, 2020, which claims priority from Japanese Patent Application No. 2019-190177 filed on Oct. 17, 2019. The contents of these applications are incorporated herein by reference in their entireties.

BACKGROUND

Technical Field

The present disclosure relates to a humidifier.

A respirator described in Patent Document 1 is provided with a blower and a humidifier. In this respirator, air force-fed from the blower enters the humidifier, and is humidified in the humidifier, and then the humidified air is sent to a patient. The humidifier is provided with a housing case in which a housing space is defined, a water storage tank housed in the housing space of the housing case, and a heater for vaporizing water stored in the tank. The tank is configured to contain water for humidifying the inside of the humidifier. Further, the tank can be taken in and out of the housing case.

Patent Document 1: Japanese Unexamined Patent Application Publication No. 2017-121502

BRIEF SUMMARY

In the humidifier described in Patent Document 1, when the tank removed is mounted inside the housing space of the housing case, the tank may be mounted in a state of being displaced with respect to the housing case. In this case, there is a possibility that displacement occurs also in a positional relationship between the tank and the heater, and water stored in the tank cannot be heated by the heater as designed.

Solution to Problem

In order to solve the above-described problem, an aspect of the present disclosure is a humidifier including a housing case, a water storage tank housed inside the housing case, and a humidification promoting mechanism configured to vaporize water stored in the tank, in which a gas humidified by the humidification promoting mechanism is discharged from the tank, wherein an attachment/detachment port for taking in and out the tank opens in the housing case, a first case hole, in addition to the attachment/detachment port, for causing an inside and an outside of the housing case to communicate with each other opens in the housing case, a first tank hole for causing an inside and an outside of the tank to communicate with each other opens in the tank, a first seal member separating a first gas flow path leading to an inside of the tank through the first case hole and the first tank hole, from an external space of the housing case is arranged between the housing case and the tank, and the first seal member, when viewed from a taking in/out direction of the tank, extends along an inner surface of the housing case, and is arranged so as to sandwich the tank from both sides in one direction orthogonal to the taking in/out direction.

According to the above configuration, first, the first seal member prevents a gas flowing through the first gas flow path from leaking outside the housing case. In addition to that, the first seal member is arranged so as to sandwich the tank from both the sides in the one direction, when viewed from the direction in which the tank is taken in and out. Thus, when the tank is housed inside the housing case, the tank is positioned in the one direction by the first seal member. Thus, it is possible to prevent the tank from being displaced in the one direction inside the housing case.

In order to solve the above-described problem, an aspect of the present disclosure is a humidifier including a housing case, a water storage tank housed inside the housing case, and a humidification promoting mechanism configured to vaporize water stored in the tank, in which a gas humidified by the humidification promoting mechanism is discharged from the tank, wherein an attachment/detachment port for taking in and out the tank opens in the housing case, a first case hole, in addition to the attachment/detachment port, for causing an inside and an outside of the housing case to communicate with each other opens in the housing case, a tank hole for causing an inside and an outside of the tank to communicate with each other opens in the tank, a first seal member separating a first gas flow path leading to an inside of the tank through the first case hole and the tank hole, from an external space of the housing case is arranged between the housing case and the tank, an elastic member is arranged between the housing case and the tank, and the elastic member, when viewed from a taking in/out direction of the tank, is arranged on a side opposite to the first seal member with the tank interposed therebetween, in one direction orthogonal to the taking in/out direction.

According to the above configuration, first, the first seal member prevents a gas flowing through the first gas flow path from leaking outside the housing case. In addition to that, the first seal member and the elastic member are arranged so as to sandwich the tank from both the sides in the one direction, when viewed from the direction in which the tank is taken in and out. Thus, when the tank is housed inside the housing case, the tank is positioned in the one direction by the first seal member and the elastic member. Thus, it is possible to prevent the tank from being displaced in the one direction inside the housing case.

It is possible to suppress displacement of a tank with respect to a housing case.

DETAILED DESCRIPTION

Hereinafter, an embodiment in which a humidifier is applied to a continuous positive airway pressure (CPAP) device will be described with reference to the figures.

First Embodiment

Figure 1:
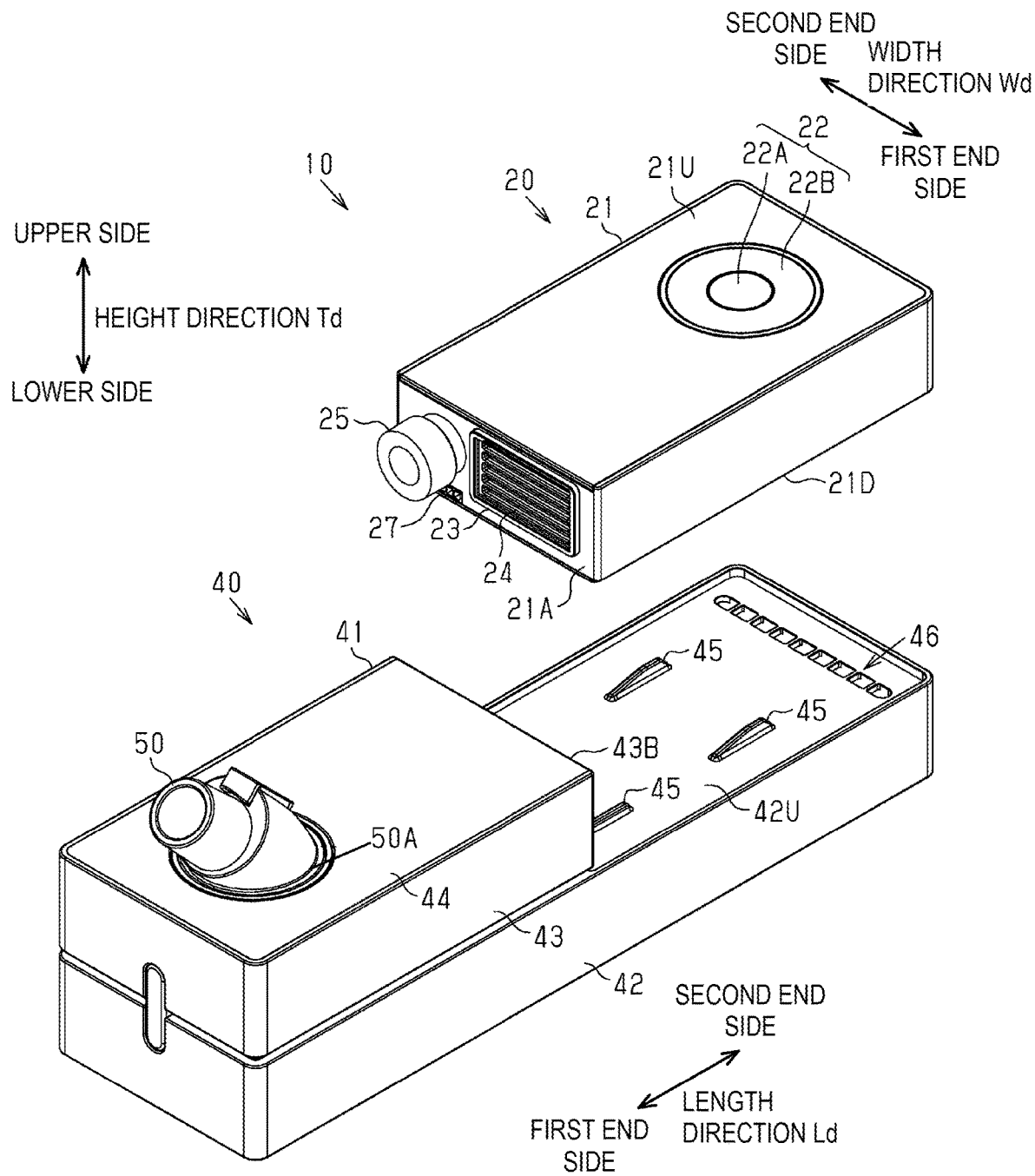
FIG. 1 is a perspective view illustrating a main body unit and a base unit of a CPAP device.
Figure 3:
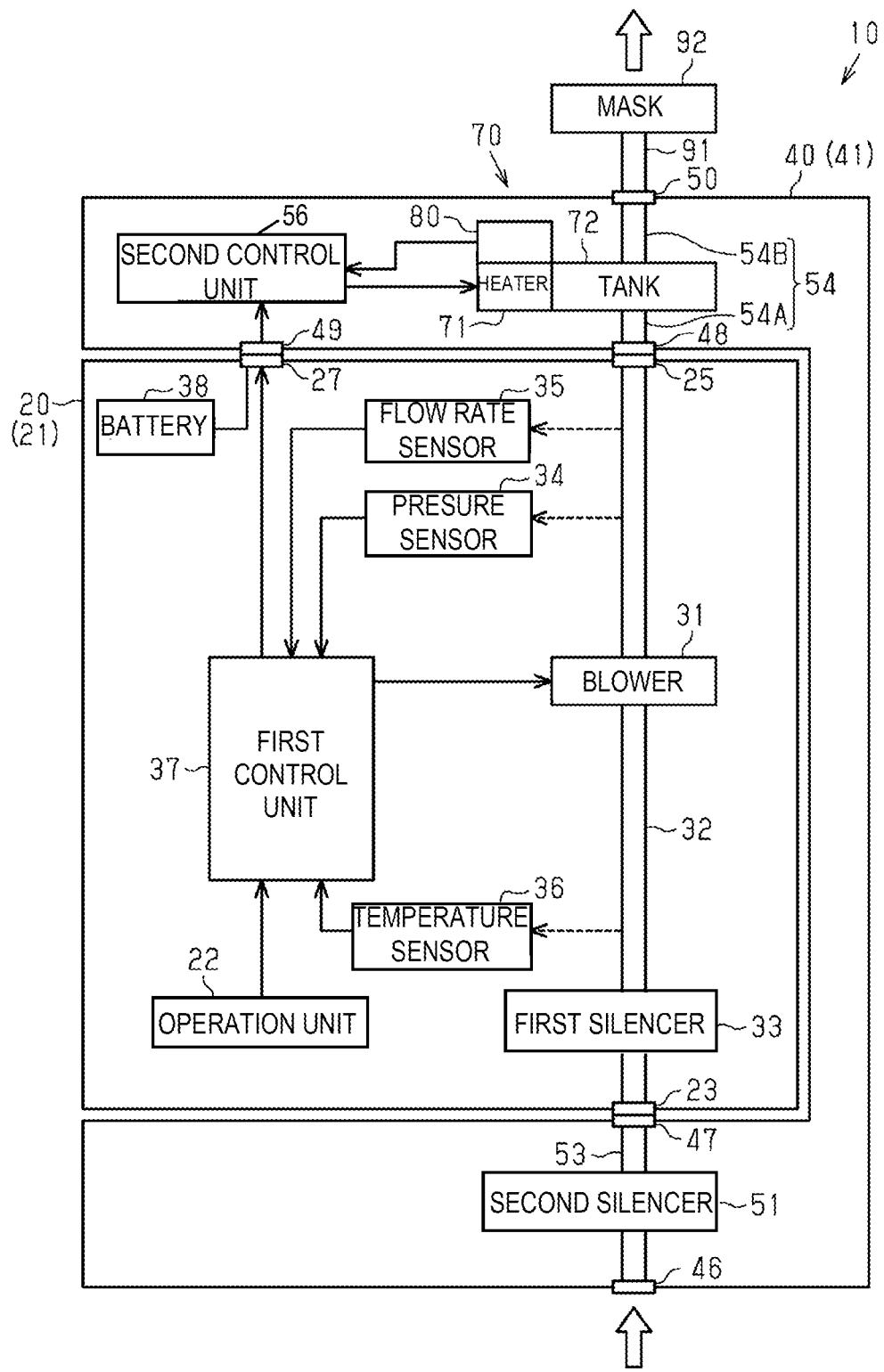
FIG. 3 is an explanatory diagram illustrating a schematic configuration of the CPAP device in the first use state.

First, a configuration of a CPAP device that sends air introduced into the device to a user's respiratory tract will be described. As illustrated in FIG. 1, a CPAP device 10 is provided with a main body unit 20 and a base unit 40. Additionally, as illustrated in FIG. 3, the main body unit 20 is provided with a blower 31 as a main constituent element. The base unit 40 is provided with a second silencer 51 and a humidifier 70 as main constituent elements.

Figure 2:
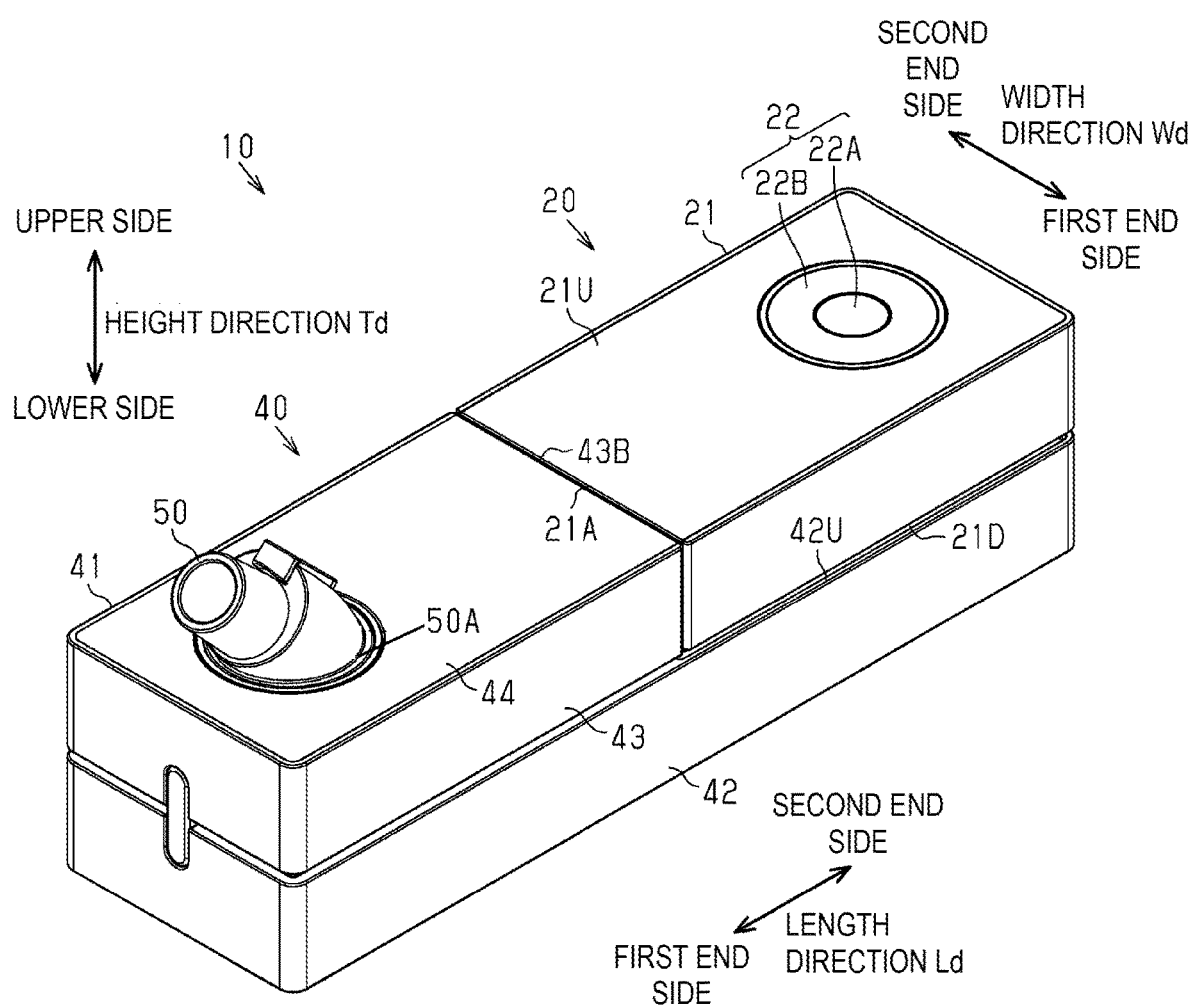
FIG. 2 is a perspective view illustrating the main body unit and the base unit of the CPAP device in a first use state.
Figure 4:
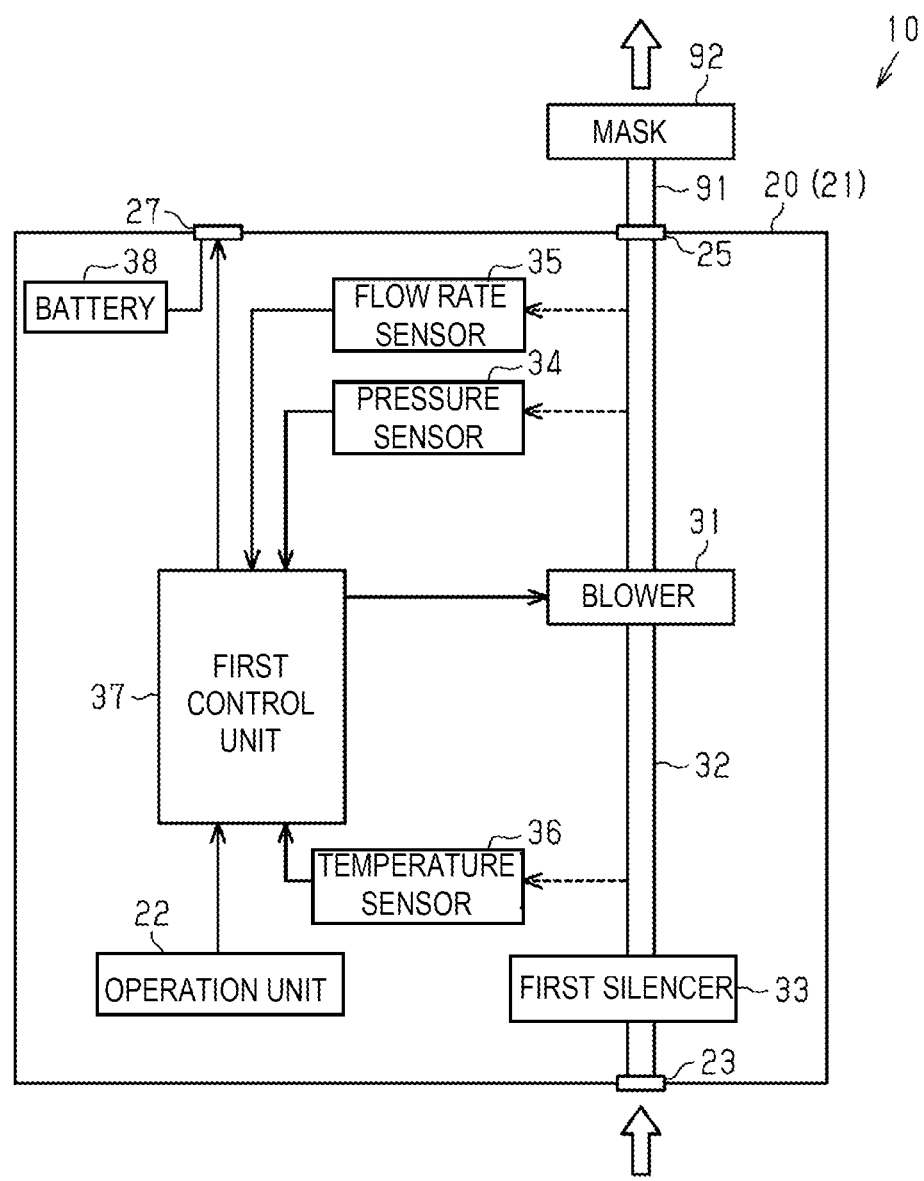
FIG. 4 is an explanatory diagram illustrating a schematic configuration of the CPAP device in a second use state.

As illustrated in FIG. 1 and FIG. 2, the main body unit 20 can be attached to and detached from the base unit 40. In the present embodiment, the CPAP device 10 is configured to be usable in a first use state and a second use state. The first use state is a state in which the main body unit 20 is loaded into the base unit 40 and used, and the second use state is a state in which the main body unit 20 is used without necessarily being loaded into the base unit 40. In other words, in the first use state, as illustrated in FIG. 3, the main body unit 20 and the base unit 40 are used. As illustrated in FIG. 4, in the second use state, only the main body unit 20 is used, and the base unit 40 is not used.

Next, a configuration of the main body unit 20 will be described.

As illustrated in FIG. 1, the main body unit 20 is provided with a first housing 21 in a flat rectangular parallelepiped shape. As illustrated in FIG. 4, the blower 31 and the like are built inside the first housing 21. Note that, in the following description, when directions related to the first housing 21 are denoted, as illustrated in FIG. 1, a thickness direction of the first housing 21 is defined as a height direction Td. In addition, a long side direction of the first housing 21 is defined as a length direction Ld, and a short side direction is defined as a width direction Wd.

As illustrated in FIG. 1, an operation unit 22 for operating the main body unit 20 is provided on an upper side surface 21U of the first housing 21. In this embodiment, the operation unit 22 is configured with a switch 22A in a circular shape, and a switch 22B in an annular shape arranged so as to surround the switch 22A. Both the switches 22A and 22B are push button switches, and operating these switches makes it possible to turn on or off a power supply of the main body unit 20, change settings, and the like.

In a first end surface 21A which is an end surface on a first end side in the length direction Ld of the first housing 21, a first introduction port 23 for introducing air from the outside to the inside of the first housing 21 opens. A filter 24 that filters dust and the like contained in the air introduced into the first housing 21 is mounted to the first introduction port 23.

As illustrated in FIG. 4, a main flow path 32 through which air flows is defined inside the first housing 21 of the main body unit 20. In the main body unit 20, an upstream end of the main flow path 32 is connected to the first introduction port 23. The blower 31 that sends out air from the first introduction port 23 to a downstream side is mounted in midstream of the main flow path 32. The blower 31 is, for example, a centrifugal fan. In the main flow path 32, a first silencer 33 is mounted between the first introduction port 23 and the blower 31. The first silencer 33 attenuates a flow sound of air that flows through the main flow path 32 along with driving of the blower 31.

A pressure sensor 34 that detects pressure of air downstream of the blower 31 in the main flow path 32 is mounted inside the first housing 21. Additionally, a flow rate sensor 35 that detects a flow rate of air downstream of the blower 31 in the main flow path 32 is mounted inside the first housing 21. Further, a temperature sensor 36 that detects a temperature of air flowing through the main flow path 32 is mounted inside the first housing 21. A first lead-out portion 25 for leading out air from the inside to the outside of the first housing 21 is connected to a downstream end of the main flow path 32.

As illustrated in FIG. 1, the first lead-out portion 25 protrudes from the first end surface 21A of the first housing 21. The first lead-out portion 25 is arranged so as to be aligned with the first introduction port 23 in the width direction Wd of the first housing 21. The first lead-out portion 25 has a cylindrical shape as a whole, and protrudes from the first end surface 21A along the length direction Ld. Then, an internal space of the first lead-out portion 25 communicates with the main flow path 32 inside the first housing 21.

In the first end surface 21A, a first connector 27 for electrically connecting the main body unit 20 to the base unit 40 is recessed. The first connector 27 is a so-called female connector, and a plurality of terminals is provided therein. The first connector 27 is arranged on a lower side of the first lead-out portion 25.

Next, an electrical configuration of the main body unit 20 of the CPAP device 10 will be described.

As illustrated in FIG. 4, the main body unit 20 is provided with a first control unit 37 for controlling operation of the blower 31. Note that, the first control unit 37 is electrically connected to the first connector 27 by wiring (not illustrated).

The first control unit 37 may be configured as circuitry including 1) one or more processors that execute various processes in accordance with a computer program (software), 2) one or more dedicated hardware circuits, such as an application-specific integrated circuit (ASIC), that execute at least some processes of the various processes, or 3) a combination thereof. The processor includes a CPU and memories, such as a RAM and a ROM, and the memory stores program codes or directives configured to cause the CPU to execute the processes. The memory or a computer-readable medium includes any available medium that can be accessed from a general purpose or dedicated computer.

In the first housing 21 of the main body unit 20, a battery 38 is provided for supplying power to the blower 31, the pressure sensor 34, the flow rate sensor 35, the temperature sensor 36, and the first control unit 37. The battery 38 is a secondary battery that can be repeatedly charged, and is charged by connecting a charging cable (not illustrated) to the main body unit 20. Further, the battery 38 is also electrically connected to the first connector 27.

The first control unit 37 is inputted with a signal indicating an operation from the operation unit 22. The first control unit 37 is inputted with a pressure value detected by the pressure sensor 34. The first control unit 37 is inputted with a flow rate value detected by the flow rate sensor 35. The first control unit 37 is inputted with a temperature value detected by the temperature sensor 36. The first control unit 37 is configured to, based on these values inputted, increase or decrease the number of rotations of the blower 31 by control such as feedback control or feed-forward control, thereby controlling an amount of air feeding and the like. For example, the first control unit 37 determines an exhalation state of a user based on values detected by the pressure sensor 34 and the flow rate sensor 35, and controls a pressure value of air to be fed to the user so as to be synchronized with the exhalation state. Further, the first control unit 37 controls power supply from the battery 38 to the first connector 27.

Next, structure of the base unit 40 will be described.

As illustrated in FIG. 1, the base unit 40 is provided with a second housing 41 in an L-shape in side view. The second housing 41 is roughly divided into a base housing 42 in a flat rectangular parallelepiped shape, and a protruding housing 43 in a flat rectangular parallelepiped shape positioned on an upper side of the base housing 42.

A dimension in a longitudinal direction of the base housing 42 is larger than a dimension in the length direction Ld of the first housing 21. A dimension in a short direction of the base housing 42 is the same as a dimension in the width direction Wd of the first housing 21. Note that, in the following description, the longitudinal direction of the base housing 42 of the second housing 41 is along the length direction Ld of the first housing 21, and the short direction of the base housing 42 is along the width direction Wd of the first housing 21.

The protruding housing 43 protrudes from an upper surface on a first end side in the length direction Ld of the base housing 42. An end on a first end side in the length direction Ld of the protruding housing 43 coincides with the end on the first end side in the length direction Ld of the base housing 42. A dimension in the height direction Td of the protruding housing 43 is substantially the same as a dimension in the height direction Td of the first housing 21. A dimension in the width direction Wd of the protruding housing 43 is substantially the same as a dimension in the width direction Wd of the first housing 21. A dimension in the length direction Ld of the protruding housing 43 is a value obtained by subtracting the dimension in the length direction Ld of the first housing 21 from the dimension in the longitudinal direction of the base housing 42.

The base housing 42 and the protruding housing 43 both have a box shape having a cavity therein. Further, an internal space of the base housing 42 and an internal space of the protruding housing 43 are continuous with each other. A wall portion of the protruding housing 43 on a side opposite to the base housing 42, that is, an upper wall portion is configured as a lid 44 that can be opened and closed. The lid 44 is removable, and with the lid 44 of the protruding housing 43 removed, the internal space of the protruding housing 43 and a part of the internal space of the base housing 42 are exposed. Note that, in FIG. 5, the base unit 40 is illustrated with the lid 44 removed.

Figure 5:
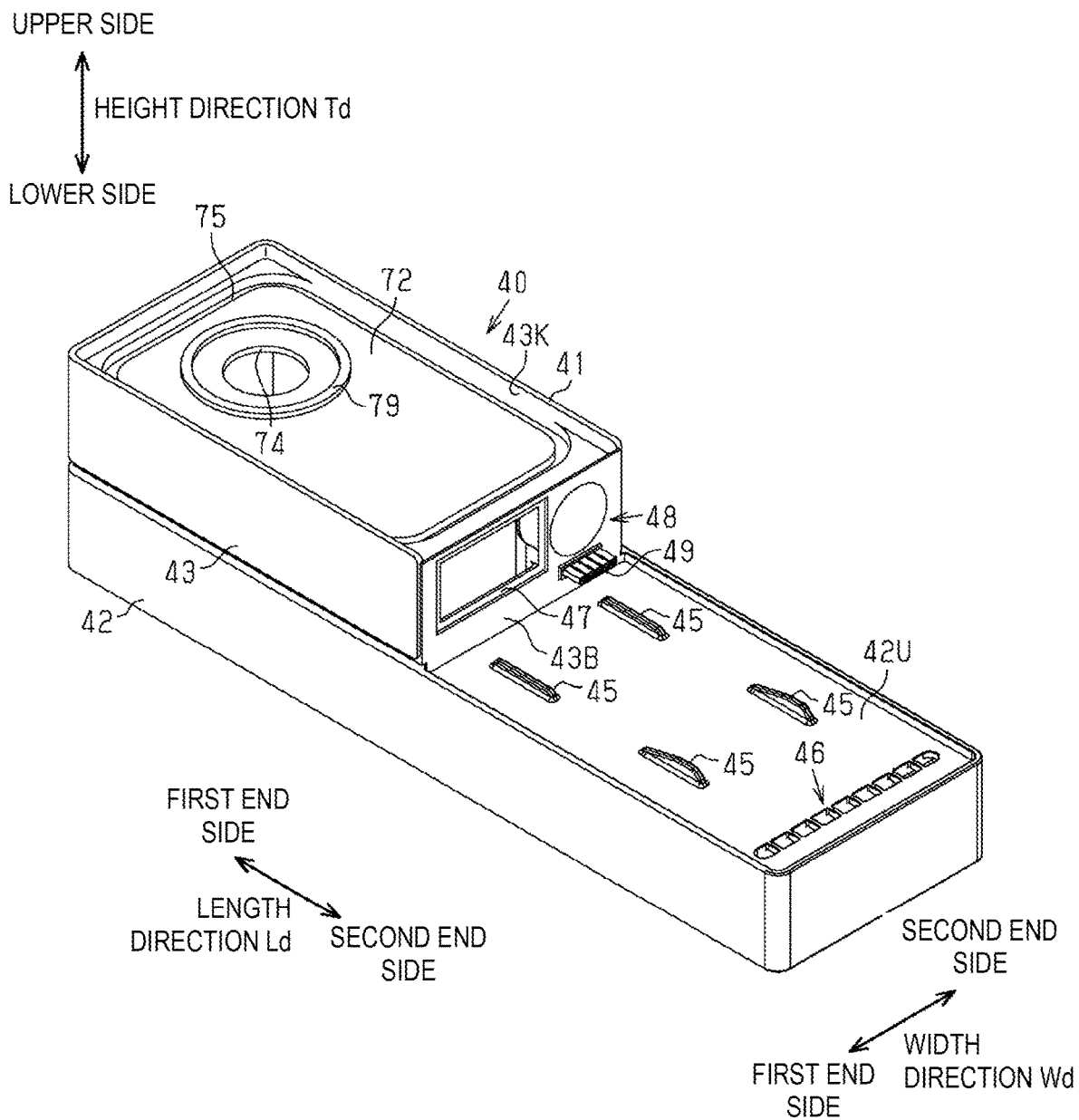
FIG. 5 is a perspective view in which the base unit is viewed from an angle different from that of FIG. 1.

As illustrated in FIG. 5, an upper side surface 42U of the base housing 42 is provided with a protrusion 45 protruding toward an upper side in the height direction Td of the base housing 42. In this embodiment, two protrusions 45 are provided for each row along the length direction Ld of the base housing 42. Then, two rows of the protrusions 45 are provided in the width direction Wd of the base housing 42. That is, in total, four protrusions 45 are provided.

In the upper side surface 42U of the base housing 42, a second introduction port 46 for introducing air from the outside to the inside of the base housing 42 opens. In the present embodiment, the second introduction ports 46 is plurally provided. The second introduction ports 46 are arranged so as to be aligned over substantially an entire region in the width direction Wd of the base housing 42. Further, each of the second introduction ports 46 is arranged in a vicinity of an edge on a second end side in the length direction Ld of the upper side surface 42U of the base housing 42. Note that, the upper side surface 42U of the base housing 42 functions as a surface for placing the main body unit 20.

As illustrated in FIG. 3, an upstream side flow path 53 through which air pulled into the blower 31 of the main body unit 20 flows is defined inside the second housing 41 of the base unit 40. In the base unit 40, an upstream end of the upstream side flow path 53 is connected to the second introduction port 46.

The second silencer 51 is mounted in midstream of the upstream side flow path 53. The second silencer 51 attenuates a flow sound of air flowing through the upstream side flow path 53. Note that, a size of volume of the second silencer 51 is larger than volume of the first silencer 33 of the main body unit 20, and a sound attenuation effect is higher than that of the first silencer 33 of the main body unit 20.

A downstream end of the upstream side flow path 53 is connected to a second lead-out port 47 for leading out air from the inside to the outside of the second housing 41. As illustrated in FIG. 5, the second lead-out port 47 opens in a surface connected to the upper side surface 42U of the base housing 42 of respective end surfaces on both sides in the length direction Ld of the protruding housing 43, that is, in a second end surface 43B which is a side surface on a second end side in the length direction Ld in the protruding housing 43. An opening shape of the second lead-out port 47 is the same as an opening shape of the first introduction port 23 of the main body unit 20.

Additionally, as illustrated in FIG. 3, a downstream side flow path 54 through which air fed from the blower 31 of the main body unit 20 flows is defined inside the second housing 41 of the base unit 40. The downstream side flow path 54 is provided with a first downstream side flow path 54A and a second downstream side flow path 54B downstream of the first downstream flow path 54A. A tank 72 of the humidifier 70 is mounted between the first downstream side flow path 54A and the second downstream side flow path 54B. In the present embodiment, the first downstream side flow path 54A functions as a first gas flow path, and the second downstream side flow path 54B functions as a second gas flow path. The humidifier 70 is provided with the tank 72 described above, a heater 71, and a heater temperature sensor 80. The tank 72 is configured to be capable of being attached to and detached from the second housing 41, and is capable of storing water therein. Air introduced inside the humidifier 70 is led out from the humidifier 70 through the tank 72, thereby humidifying the air. The heater 71 heats water in the tank 72. The heater temperature sensor 80 detects a temperature of the heater 71.

As illustrated in FIG. 5, a third introduction hole 48 for introducing air from the outside to the inside of the protruding housing 43 opens in the second end surface 43B of the protruding housing 43 in the base unit 40. The third introduction hole 48 is arranged so as to be aligned with the first lead-out portion 25 in the width direction Wd in the protruding housing 43. The third introduction hole 48 has a circular shape in plan view, and an outer diameter of the third introduction hole 48 is larger than an outer diameter of the first lead-out portion 25 in the first housing 21.

In the second end surface 43B, a second connector 49 for electrically connecting the main body unit 20 to the base unit 40 protrudes. The second connector 49 is a so-called male connector corresponding to a shape of the first connector 27 described above, and is provided with a plurality of terminals therein. The second connector 49 is arranged on a lower side of the third introduction hole 48.

As illustrated in FIG. 1, a cylindrical third lead-out portion 50 for leading out air from the inside to the outside of the second housing 41 protrudes from the lid 44 of the second housing 41. A central axis line of the third lead-out portion 50 is inclined with respect to the height direction Td in the protruding housing 43. An internal space of the third lead-out portion 50 communicates with the downstream side flow path 54.

Next, an electrical configuration of the CPAP device 10 in the base unit 40 will be described.

As illustrated in FIG. 3, the base unit 40 is provided with a second control unit 56 that controls operation of the heater 71. The second control unit 56 may be configured as circuitry including 1) one or more processors that execute various processes in accordance with a computer program (software), 2) one or more dedicated hardware circuits, such as an application-specific integrated circuit (ASIC), that execute at least some processes of the various processes, or 3) a combination thereof. The processor includes a CPU and memories, such as a RAM and a ROM, and the memory stores program codes or directives configured to cause the CPU to execute the processes. The memory or a computer-readable medium includes any available medium that can be accessed from a general purpose or dedicated computer.

Electric power is supplied to the second control unit 56 from the battery 38 of the main body unit 20 with the first connector 27 of the main body unit 20, and the second connector 49 interposed therebetween. Additionally, a signal indicating a temperature value of air detected by the temperature sensor 36 is inputted from the first control unit 37 to the second control unit 56 with the first connector 27 of the main body unit 20, and the second connector 49 interposed therebetween.

The second control unit 56 sets a target heater temperature for heating water in the tank 72, based on the inputted air temperature value. For example, the second control unit 56 sets the target heater temperature with a predetermined calculation formula. Then, the second control unit 56 is configured to drive the heater 71, based on a heater temperature detected by the heater temperature sensor 80 so as to set the heater temperature to the target heater temperature by control such as feedback control or feed-forward control. The second control unit 56 adjusts a water temperature in the tank 72 by the heater 71. Then, when the heater temperature reaches the target heater temperature, the second control unit 56 controls the heater 71 so as to maintain the heater temperature at the target heater temperature.

Next, internal structure of the base unit 40, particularly the humidifier 70, will be described in detail.

Figure 6:
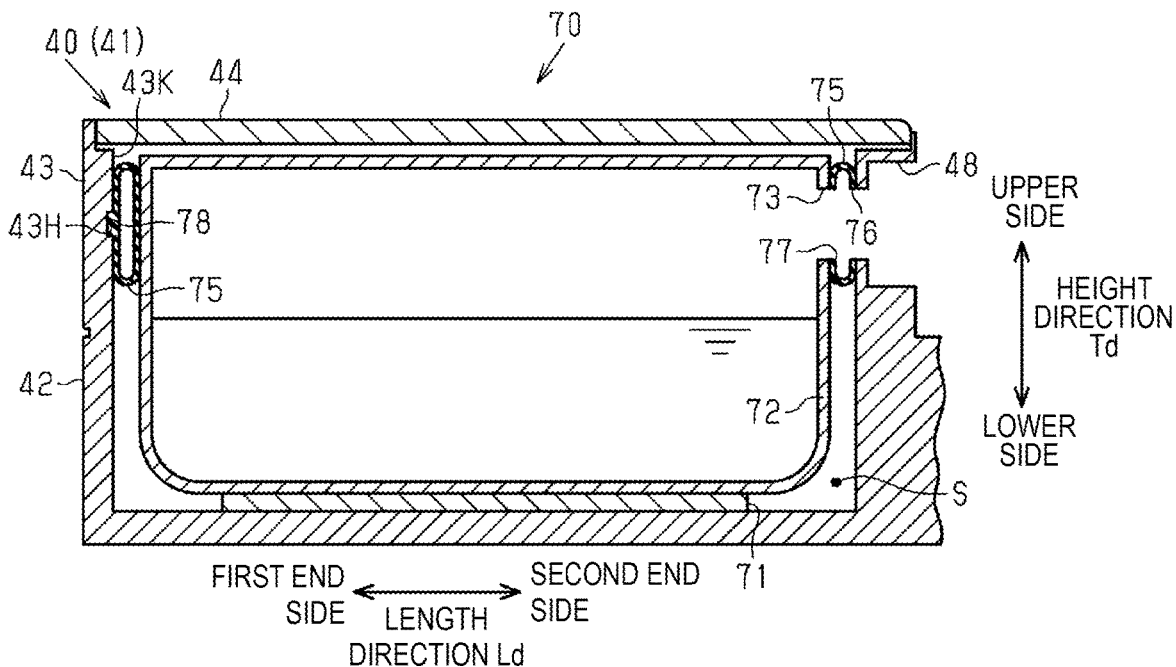
FIG. 6 is an end view of the base unit.

As illustrated in FIG. 6, a housing space S in a rectangular parallelepiped shape is defined by the internal space of the base housing 42 and the internal space of the protruding housing 43. With the lid 44 of the base unit 40 removed, an upper side of the protruding housing 43 opens as an attachment/detachment port 43K. The heater 71 in a plate shape is arranged on a part of the base unit 40 on a side opposite to the attachment/detachment port 43K, that is, on a bottom of the base housing 42. In the housing space S, the water storage tank 72 is housed on an upper side in the height direction Td of the heater 71. The tank 72 has a substantially rectangular parallelepiped shape. Water stored in the tank 72 is heated by the heater 71, and vaporization is promoted. In the present embodiment, the second housing 41 functions as a housing case, and the heater 71 functions as a humidification promoting mechanism.

With the lid 44 open, the tank 72 is taken in to the housing space S, which is an internal space of the second housing 41, from the attachment/detachment port 43K that opens upward in the height direction Td of the protruding housing 43, and is taken out from the housing space S of the second housing 41. Here, a direction in which the tank 72 is taken in to and out from the attachment/detachment port 43K is defined as a taking in/out direction. In the present embodiment, the taking in/out direction coincides with a vertical direction, and also coincides with the height direction Td in the second use state.

As illustrated in FIG. 6, a first tank hole 73 in a circular shape in plan view for supplying air to the tank 72 opens in a wall portion on a second end side in the length direction Ld of the tank 72. The first tank hole 73 causes the inside and the outside of the tank 72 to communicate with each other. A position of the first tank hole 73 coincides with a position of the third introduction hole 48, when viewed from the length direction Ld. The third introduction hole 48 causes the inside and the outside of the base housing 42 to communicate with each other. That is, in the present embodiment, the third introduction hole 48 functions as a first case hole.

A first seal member 75 made of synthetic rubber is arranged between the tank 72 and the protruding housing 43. The first seal member 75 is arranged in an annular shape so as to entirely surround the tank 72, when viewed from the height direction Td. That is, the first seal member 75 extends along an inner surface of the protruding housing 43, and is arranged so as to sandwich the tank 72 from both sides in any direction orthogonal to the taking in/out direction.

A dimension in the height direction Td of the first seal member 75 is larger than respective dimensions in the height direction Td of the first tank hole 73 and the third introduction hole 48. Further, a position in the height direction Td of the first seal member 75 is set such that a center in the height direction Td of the first seal member 75 coincides with a center in the height direction Td of the first tank hole 73 and a center in the height direction Td of the third introduction hole 48.

Further, the first seal member 75 has a hollow shape. A first through-hole 76 in a circular shape in plan view and serving as a communication hole penetrates a part of the first seal member 75 that faces the third introduction hole 48. The first through-hole 76 causes an internal space of the first seal member 75 and an external space on a side of the third introduction hole 48 to communicate with each other. Similarly, a second through-hole 77 in a circular shape in plan view penetrates a part of the first seal member 75 that faces the first tank hole 73. The second through-hole 77 causes the internal space of the first seal member 75 and an internal space in the tank 72 to communicate with each other.

The first seal member 75 is provided with a second fitting portion 78 protruding outward in a convex shape from an outer peripheral surface of an annular portion of the first seal member 75, when viewed from the height direction Td. The second fitting portion 78 is in a substantially quadrangular shape in a sectional view.

A first fitting portion 43H for fixing a position of the first seal member 75 is recessed in an inner surface of the protruding housing 43. When viewed from the height direction Td, the first fitting portion 43H extends along substantially an entirety of the inner surface of the protruding housing 43 except for a position of the third introduction hole 48. A position in the height direction Td of the first fitting portion 43H is the same position as a position in the height direction Td of the third introduction hole 48. The first fitting portion 43H is in a substantially quadrangular shape corresponding to the second fitting portion 78 in a sectional view. The second fitting portion 78 of the first seal member 75 is fitted into this first fitting portion 43H.

As illustrated in FIG. 5, a second tank hole 74 penetrates a wall portion on an upper side in the height direction Td of the tank 72. The second tank hole 74 causes the inside and the outside of the tank 72 to communicate with each other. The second tank hole 74 is, with the lid 44 closed, arranged at a position facing a lid hole 50A which is an opening on a lid side of the third lead-out portion 50 of the lid 44 illustrated in FIG. 1.

As illustrated in FIG. 5, a second seal member 79 in an annular shape is arranged on an upper side in the height direction Td of the tank 72 so as to surround an opening edge of the second tank hole 74. With the lid 44 mounted, the second seal member 79 is sandwiched between the wall portion on the upper side of the tank 72 and the lid 44. Thus, the second seal member 79 that separates the second downstream side flow path 54B leading to the inside of the tank 72 through the lid hole 50A and the second tank hole 74, from the housing space S, is arranged between the tank 72 and the lid 44.

Next, an action of the CPAP device 10 in the first use state will be described.

Figure 7:
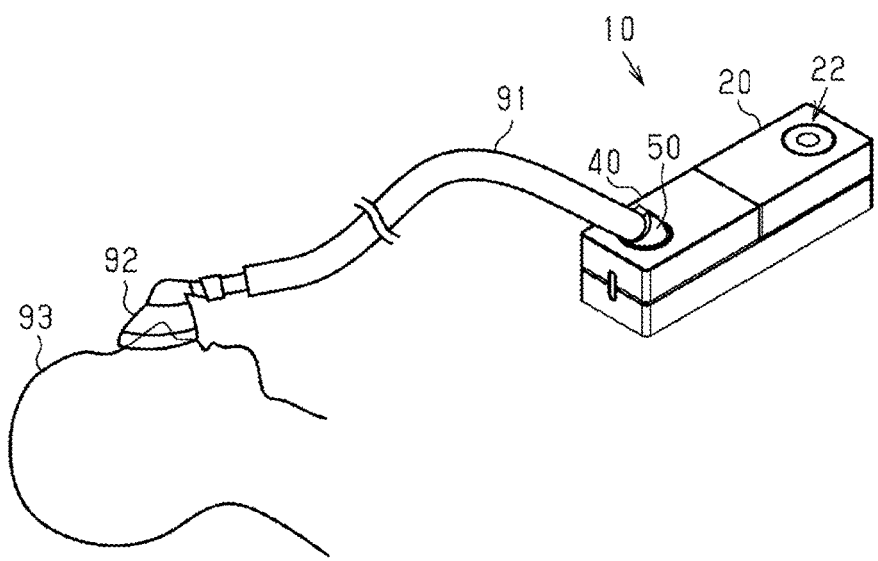
FIG. 7 is a schematic view illustrating the first use state of the CPAP device.

As illustrated in FIG. 7, in the first use state, the main body unit 20 is in a state of being loaded into the base unit 40. To be specific, as illustrated in FIG. 2, the main body unit 20 is placed on the base unit 40 such that a lower side surface 21D in the first housing 21 faces the upper side surface 42U of the base housing 42 in the second housing 41. Further, the first end surface 21A in the first housing 21 and the second end surface 43B of the protruding housing 43 in the second housing 41 face and are in contact with each other. Thus, in the first use state, the CPAP device 10 has an elongated thin rectangular parallelepiped shape as a whole. Note that, in the present embodiment, in the first use state in which the base unit 40 is used to use the CPAP device 10, the protruding housing 43 is used in a direction in which the protruding housing 43 is positioned on an upper side in the vertical direction of the base housing 42.

As illustrated in FIG. 3, in the first use state, the first introduction port 23 of the first housing 21 is connected to the second lead-out port 47 of the second housing 41, and the upstream end of the main flow path 32 of the main body unit 20 is connected to the downstream end of the upstream side flow path 53 of the base unit 40 with these first introduction port 23 and second lead-out port 47 interposed therebetween. In addition, the first lead-out portion 25 of the first housing 21 is inserted into the third introduction hole 48 of the second housing 41, and the downstream end of the main flow path 32 of the main body unit 20 is connected to an upstream end of the downstream side flow path 54 of the base unit 40 with these first lead-out portion 25 and third introduction hole 48 interposed therebetween.

As illustrated in FIG. 7, in the first use state, a first end portion of an air tube 91 is connected to the third lead-out portion 50 of the base unit 40, and a second end portion of the air tube 91 is connected to a mask 92. The mask 92 is worn, for example, so as to cover a nose or mouth of a user 93.

In the first use state of the CPAP device 10, when the operation unit 22 of the main body unit 20 is operated and the power supply of the main body unit 20 is turned on, the blower 31 is driven. Here, due to the protrusion 45 provided on the upper side surface 42U of the base housing 42 of the base unit 40, a gap is generated between the lower side surface 21D of the first housing 21 and the second introduction port 46. Thus, air is pulled inside the CPAP device 10 from this gap through the second introduction port 46. The air pulled inside the CPAP device 10 is discharged outside from the third lead-out portion 50 of the second housing 41, through the upstream side flow path 53 of the second housing 41, the main flow path 32 of the first housing 21, and the downstream side flow path 54 of the second housing 41. Thereby, the air is fed through the air tube 91 and the mask 92 into a respiratory tract of the user 93.

Here, particularly in the downstream side flow path 54, as illustrated in FIG. 6, first, air pressurized by the blower 31 is introduced from the third introduction hole 48. The air flowing through the third introduction hole 48, which is an opening on a tank side of the third introduction hole 48, flows from the first through-hole 76 of the first seal member 75 into the internal space of the first seal member 75, passes through the second through-hole 77, and flows inside the tank 72 from the first tank hole 73. The air flowing inside the tank 72 is humidified, and discharged from the third lead-out portion 50, via the second tank hole 74 and the lid hole 50A from the inside of the tank 72 which is the second downstream side flow path 54B. At this time, a part of the air flowing through the first downstream side flow path 54A also flows into the internal space of the first seal member 75, and the first seal member 75 tries to expand.

Next, the CPAP device in the second use state will be described.

Figure 8:
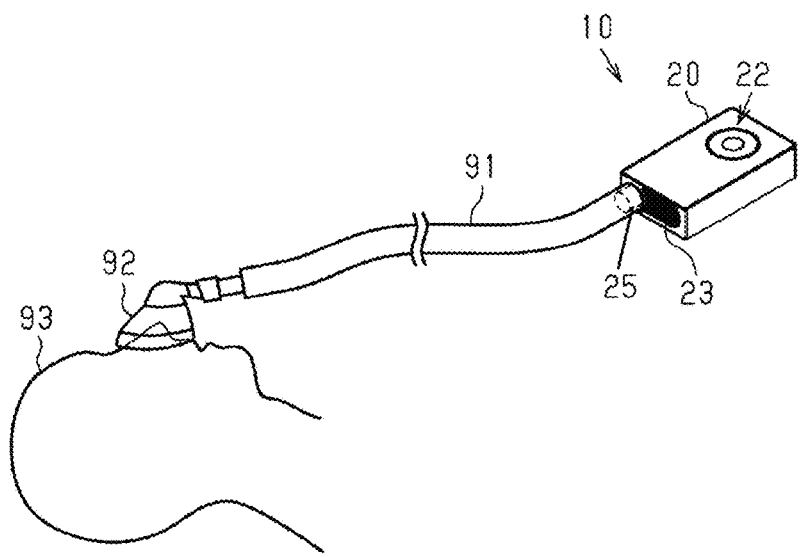
FIG. 8 is a schematic view illustrating the second use state of the CPAP device.

As illustrated in FIG. 8, in the second use state, the main body unit 20 is not loaded into the base unit 40, that is, the CPAP device 10 is used only with the main unit 20. In this case, the first end portion of the air tube 91 is connected to the first lead-out portion 25 of the main body unit 20, and the second end portion of the air tube 91 is connected to the mask 92. The mask 92 is worn, for example, so as to cover the nose or mouth of the user 93. In the present embodiment, the humidifier 70 does not function in the second use state.

Next, effects of the humidifier 70 in the above first embodiment will be described.

(1) In the above first embodiment, in the CPAP device 10, when the blower 31 of the main body unit 20 is driven in the first use state, air flows from the main flow path 32 of the main body unit 20 to the downstream side flow path 54 of the base unit 40. According to the above first embodiment, first, the first seal member 75 prevents the air flowing from the main flow path 32 to the downstream side flow path 54 from leaking outside the main body unit 20 and the base unit 40. That is, the first seal member 75 exhibits a sealing function.

Figure 9:
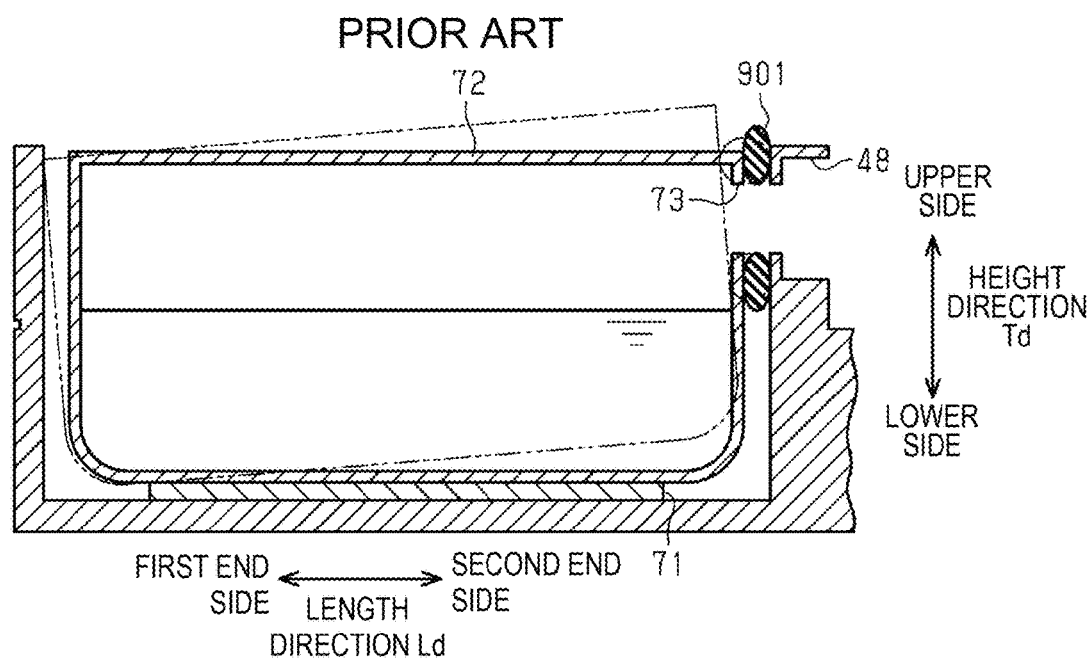
FIG. 9 is an end view of a base unit to be compared.

Incidentally, as illustrated in FIG. 9, it is assumed that an O-ring 901 in an annular shape surrounding the first tank hole 73 when viewed from the length direction Ld is employed, as a configuration for preventing the air flowing from the main flow path 32 to the downstream side flow path 54 from leaking outside the main body unit 20 and the base unit 40. In this case, the O-ring 901 presses the tank 72 from a second end side toward a first end side in the length direction Ld when viewed from a direction in which the tank 72 is taken in and out. Thus, as indicated by a two-dot chain line in FIG. 9, there is a possibility that the tank 72 is inclined due to pressing force of the O-ring 901. As a result, a bottom surface of the tank 72 is partially separated from the heater 71, and it becomes difficult for water in the tank 72 to be heated by the heater 71.

In this regard, in the above first embodiment, the first seal member 75 has an annular shape when viewed from a direction in which the tank 72 is taking in/out, and surrounds an entire circumference of the tank 72. Thus, as illustrated in FIG. 6, the first seal member 75 sandwiches the tank 72 from both sides not only in one direction orthogonal to the vertical direction, but also in any direction orthogonal to the vertical direction, when viewed from the direction in which the tank 72 is taken in and out. Thus, when the tank 72 is housed in the housing space S of the base housing 42, the tank 72 is positioned in any direction orthogonal to the vertical direction by the first seal member 75. Thus, it is possible to suppress displacement of the tank 72 in the housing space S of the base housing 42. Moreover, the configuration for this positioning is realized by the first seal member 75 for preventing air from leaking outside. Thus, an increase in the number of components for positioning the tank 72 can also be prevented.

(2) According to the above first embodiment, the first seal member 75 has a hollow shape. Thus, air flowing from the main flow path 32 to the downstream side flow path 54 also flows into the internal space of the first seal member 75. When pressurized air is fed into the internal space of the first seal member 75, the first seal member 75 tries to expand. Then, the first seal member 75 trying to expand presses the tank 72, thus positioning of the tank 72 can be made more reliable.

Note that, when the tank 72 is housed in the housing space S of the base housing 42, pressurized air does not flow into the internal space of the first seal member 75, and thus the first seal member 75 does not try to expand. Thus, when the removed tank 72 is housed in the housing space S from the attachment/detachment port 43K, the first seal member 75 does not excessively press the tank 72, and the tank 72 is easily inserted.

(3) According to the above first embodiment, the material for the first seal member 75 is synthetic rubber. Thus, first, force for pressing the tank 72 when the first seal member 75 tries to expand is relatively large, and thus reliable positioning of the tank 72 is further easily realized. On the other hand, when rigidity of the first seal member 75 is excessively high, and the tank 72 is housed in the housing space S of the base housing 42, it is difficult to take in the tank 72 due to high resistance. In this regard, since the material for the first seal member 75 is synthetic rubber, it is easy to prevent the resistance when the tank 72 is housed in the housing space S of the base housing 42 from increasing excessively. As a result, it is possible to achieve ease of insertion when the tank 72 is housed, and reliable positioning of the tank 72, in a compatible manner.

(4) According to the above first embodiment, when the second fitting portion 78 is fitted into the first fitting portion 43H, the first seal member 75 is positioned with respect to the base housing 42. Here, the first seal member 75 positions the tank 72 by pressing the tank 72. Thus, there is a possibility that, when a position of the first seal member 75 with respect to the base housing 42 is displaced from a designed position, a position of the tank 72 with respect to the base housing 42 is also displaced. In this regard, according to the above first embodiment, since the first seal member 75 is positioned with respect to the base housing 42, the position of the tank 72 positioned by the first seal member 75 is also less likely to be displaced from the designed position.

(5) According to the above first embodiment, in the first use state, the air tube 91 is mounted to the third lead-out portion 50 of the lid 44. By opening and closing the lid 44, the tank 72 can be taken out from the attachment/detachment port 43K. At this time, the air tube 91 can be kept mounted to the lid 44. Accordingly, in a case of being used continuously in the first use state, even when the tank 72 is repeatedly attached and detached, the air tube 91 need not be detached.

Second Embodiment

Next, a second embodiment in which a humidifier is applied to a CPAP device will be described. Note that, in the following description of the second embodiment, a configuration similar to that of the first embodiment is assigned the same reference numeral, and a specific description thereof will be omitted or simplified.

Figure 10:
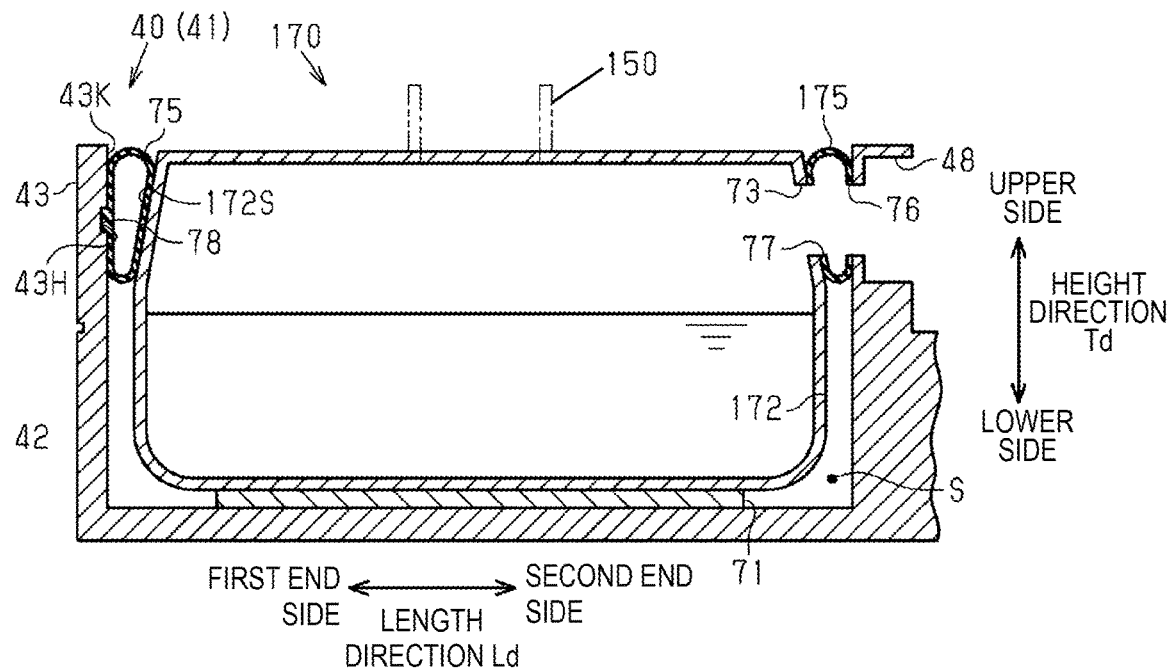
FIG. 10 is an end view of a base unit in a second embodiment.

As illustrated in FIG. 10, in a humidifier 170, an upper side of the protruding housing 43 opens as the attachment/detachment port 43K. Note that, in this second embodiment, the lid 44 in the first embodiment is not provided, and the attachment/detachment port 43K is always in a state of being open. A third lead-out portion 150 is mounted to an upper wall portion of a tank 172. The third lead-out portion 150 has a cylindrical shape, and causes the inside and the outside of the tank 172 to communicate with each other.

A contact surface 172S of an outer surface of the tank 172 that is in contact with a first seal member 175 is inclined so as to approach an inner wall of the second housing 41 as a distance to a lower side in the height direction Td decreases. In addition, the contact surface 172S faces a side of the attachment/detachment port 43K in a taking in/out direction of the tank 172. Then, the first seal member 175 is in contact with the contact surface 172S on an upper side in the height direction Td, which is the taking in/out direction of the tank 172. Further, a surface of the first seal member 175 that is in contact with the contact surface 172S is inclined so as to approach the tank 172 as a distance to an upper side in the height direction Td decreases. Then, the first seal member 175 fills a space between the tank 172 and the inner wall of the second housing 41.

Next, an action of the humidifier 170 in the second embodiment will be described.

In a first use state of the CPAP device 10, the tank 172 is housed in the second housing 41, and the air tube 91 is mounted to the third lead-out portion 150 of the tank 172. Then, air humidified in the humidifier 170 is fed from the third lead-out portion 150 to a respiratory tract of the user 93 through the air tube 91.

Here, when a part of the air flowing through the first downstream side flow path 54A flows into an internal space of the first seal member 175, and the first seal member 175 tries to expand, the contact surface 172S of the tank 172 is pressed by the first seal member 175. As a result, the tank 172 is pressed toward a lower side in the height direction Td, which is the taking in/out direction of the tank 172.

Next, effects of the humidifier 170 in the second embodiment will be described. In the second embodiment, in addition to the effects (1) to (4) of the above first embodiment, the following effects are exhibited.

(6) According to the second embodiment, when the first seal member 175 tries to expand, the contact surface 172S of the tank 172 is pressed, and thus the tank 172 as a whole is pressed toward the lower side in the height direction Td, which is the taking in/out direction of the tank 172. Here, in the present embodiment, the heater 71 for heating water in the tank 172 is arranged at a bottom of the tank 172. Thus, the first seal member 175 performs positioning also in the height direction Td such that the tank 172 is in contact with the heater 71. As a result, since the tank 172 and the heater 71 are in contact with each other, it is possible to prevent insufficient heating of water stored in the tank 172 by the heater 71, and insufficient humidification of air supplied to the user 93.

(7) According to the second embodiment, the third lead-out portion 150 is directly mounted to the tank 172, thus, by replacing the tank 172, the third lead-out portion 150 is also replaced together. Thus, for example, when used by a new user 93, by replacing the tank 172, the third lead-out portion 150 can also be replaced at the same time, thus, the new user 93 can use the CPAP device 10 as a clean CPAP device 10.

Third Embodiment

Next, a third embodiment in which a humidifier is applied to a CPAP device will be described. In this third embodiment, the configuration of the humidifier 70 in the first embodiment is partially changed. Note that, in the following description of the third embodiment, a configuration similar to that of the first embodiment is assigned the same reference numeral, and a specific description thereof will be omitted or simplified.

Figure 11:
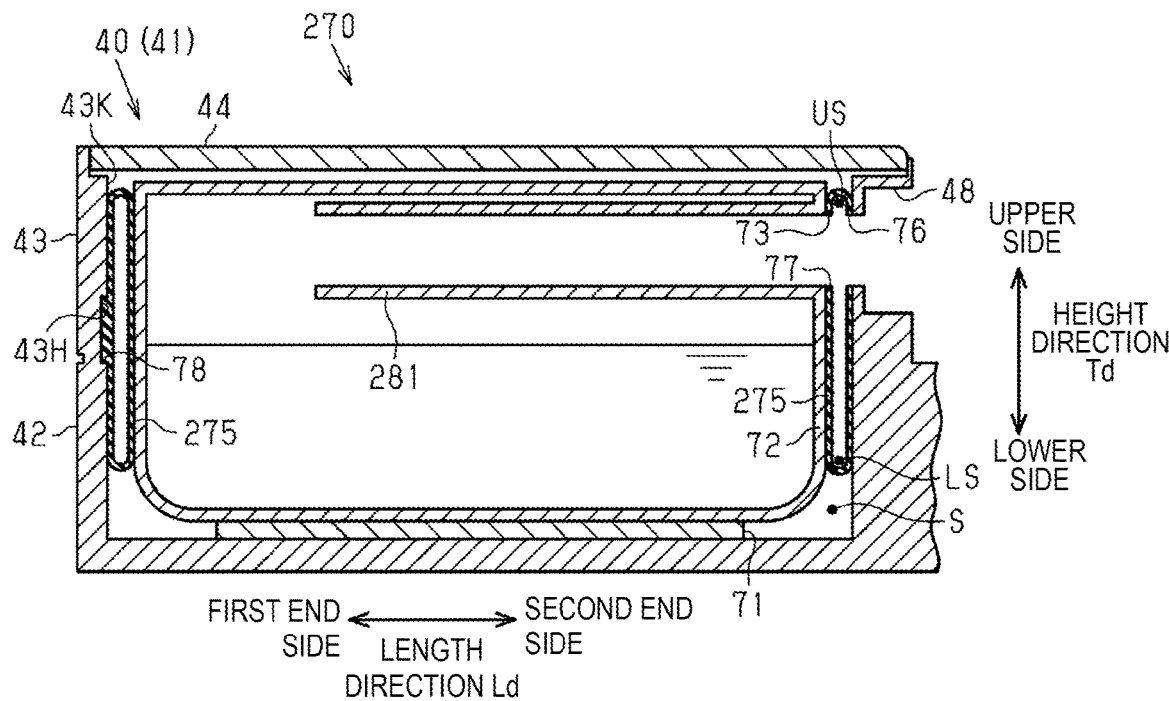
FIG. 11 is an end view of a base unit in a third embodiment.

As illustrated in FIG. 11, in the tank 72 of a humidifier 270, an in-tank flow path portion 281 in a cylindrical shape extends from an opening edge of the first tank hole 73 of the tank 72 toward the inside of the tank 72. An opening of the in-tank flow path portion 281 on a side opposite to the first tank hole 73 extends closer to a first end side than a center of the tank 72 in the length direction Ld. On the other hand, a tip end of the in-tank flow path portion 281 does not reach an inner wall of the tank 72. That is, the in-tank flow path portion 281 opens inside the tank 72.

In this third embodiment, a dimension in the height direction Td of the first seal member 275 is close to a dimension in a vertical direction of the tank 72. Here, in an internal space of the first seal member 275, a space closer to a side of the attachment/detachment port 43K than the first tank hole 73 is defined as an upper side space US, and a space closer to a bottom side of the tank 72 than the first tank hole 73 is defined as a lower side space LS. In this case, a distance from the first tank hole 73 to a lower end of the lower side space LS is larger than a distance from the first tank hole 73 to an upper end of the upper side space US. In the present embodiment, the upper side space US and the lower side space LS have the same dimension in a direction perpendicular to the height direction Td. As a result, volume of the lower side space LS is larger than volume of the upper side space US.

Next, an action and effects of the humidifier 270 in the third embodiment will be described. In the third embodiment, in addition to the effects (1) to (5) of the above first embodiment, the following effects are exhibited.

(8) In the above third embodiment, the humidifier 270 is applied to the CPAP device 10. As illustrated in FIG. 7, the CPAP device 10 is connected to the user 93 with the air tube 91 and the mask 92 interposed therebetween. Then, the CPAP device 10 is used to supply fluid to the user 93 for a sleep-related therapy such as obstructive sleep apnea (OSA) syndrome. The CPAP device 10 supplies air at a pressure higher than atmospheric pressure from the blower 31 to the mask 92 worn on a mouth or nose of the user 93 to open a respiratory tract. Thus, when the user 93 turns over during sleep, or the like, an entirety of the CPAP device 10 is inclined in some cases. Thus, the second housing 41 functioning as a housing case is also inclined in some cases.

In the above third embodiment, in the tank 72, the in-tank flow path portion 281 extends inward the tank 72 from the first tank hole 73. Thus, even when the second housing 41 is inclined such that a second end side in the length direction Ld goes to a lower side, an opening of the in-tank flow path portion 281 on a side of the tank 72 is positioned on an upper side than a water level in the tank 72. Thus, water in the tank 72 is less likely to flow into the in-tank flow path portion 281, thus flowing of the water in the tank 72 into the main body unit 20 is suppressed.

(9) In the above third embodiment, in the internal space of the first seal member 275, the volume of the lower side space LS is larger than the volume of the upper side space US. Thus, even when water in the tank 72 flows into the first seal member 275 from the first tank hole 73, the water is likely to pool in the lower side space LS of the first seal member 275. Thus, flowing of water from the first through-hole 76 of the first seal member 275 into the main body unit 20 is suppressed.

Fourth Embodiment

Next, a fourth embodiment in which a humidifier is applied to a CPAP device will be described. In this fourth embodiment, the configuration of the humidifier 70 in the first embodiment is partially changed. Note that, in the following description of the fourth embodiment, a configuration similar to that of the first embodiment is assigned the same reference numeral, and a specific description thereof will be omitted or simplified.

Figure 12:
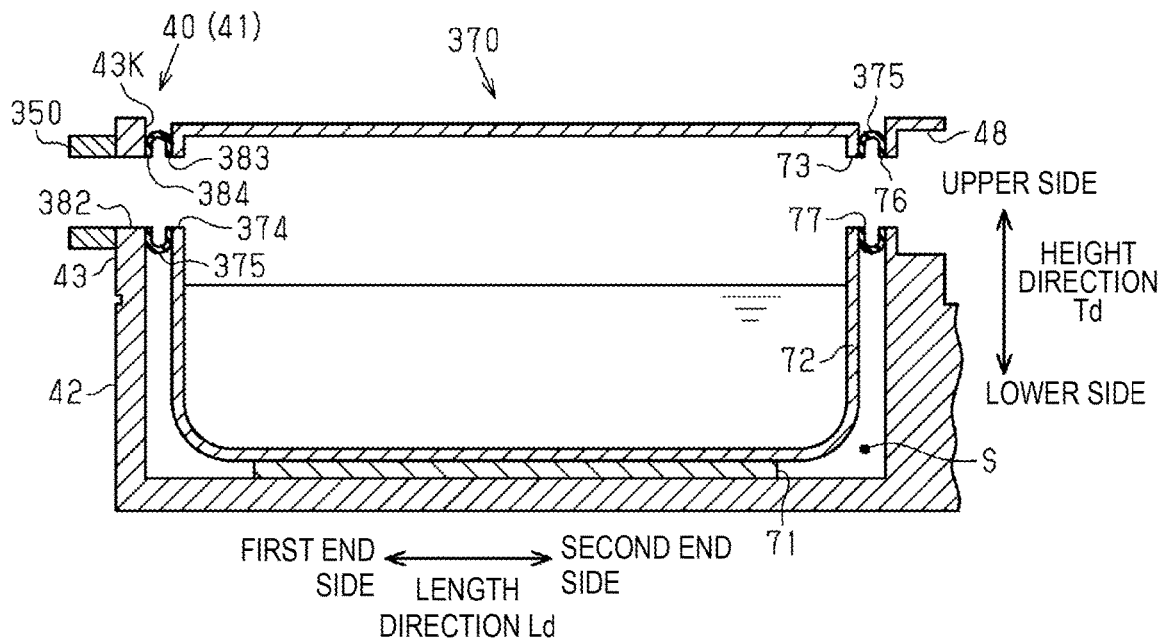
FIG. 12 is an end view of a base unit in a fourth embodiment.

As illustrated in FIG. 12, in a humidifier 370, an upper side of the protruding housing 43 opens as the attachment/detachment port 43K. Note that, in this fourth embodiment, the lid 44 in the first embodiment is not provided, and the attachment/detachment port 43K is always in a state of being open.

A second tank hole 374 in a circular shape in plan view for discharging humidified air from the tank 72 penetrates a wall portion on a first end side in the length direction Ld of the tank 72 of the humidifier 370. The second tank hole 374 causes the inside and the outside of the tank 72 to communicate with each other. The second tank hole 374 is arranged at the same position as that of a first seal member 375 in the height direction Td.

Additionally, an exhaust side case hole 382 in a circular shape in plan view that functions as a second case hole opens in a wall portion on the first end side in the length direction Ld of the second housing 41. The exhaust side case hole 382 causes the inside and the outside of the second housing 41 to communicate with each other. In addition, a position of the exhaust side case hole 382 coincides with that of the second tank hole 374 in the height direction Td and the width direction Wd. Then, a third lead-out portion 350 in a cylindrical shape is mounted to an outer side portion of the second housing 41 of the exhaust side case hole 382. The third lead-out portion 350 extends toward the first end side in the length direction Ld.

The first seal member 375 is arranged between the second tank hole 374 and the exhaust side case hole 382. In addition, of the first seal member 375, a third through-hole 383 penetrates at a position facing the second tank hole 374, and a fourth through-hole 384 penetrates at a position facing the exhaust side case hole 382. Then, the first seal member 375 separates the second downstream side flow path 54B leading to the inside of the tank 72 through the exhaust side case hole 382 and the second tank hole 374, from an external space of the second housing 41. That is, the first seal member 375 separates not only the first downstream side flow path 54A from the external space of the second housing 41, but also the second downstream side flow path 54B from the external space of the second housing 41.

Next, an action and effects of the humidifier 370 in the fourth embodiment will be described. In the fourth embodiment, in addition to the effects (1) to (4) of the above first embodiment, the following effects are exhibited.

(10) According to the fourth embodiment, the third lead-out portion 350 is arranged without necessarily protruding to an upper side of the second housing 41. Thus, the CPAP device 10 can be reduced in height.

(11) According to the above fourth embodiment, the first seal member 375 has, in addition to the function of separating the first downstream side flow path 54A from the external space of the second housing 41, the function of separating the second downstream side flow path 54B from the external space of the second housing 41. Thus, a function of sealing an upstream side and a downstream side of the tank 72 can be achieved by a single member. Thus, the number of components of the humidifier 370 can be reduced.

Each of the above embodiments can be modified and implemented as follows. Each embodiment, and modifications described below can be combined and implemented within a range where technical inconsistency does not occur.

In each of the embodiments, the configuration of the second housing 41 functioning as the housing case is not limited to the example of each embodiment described above. It is sufficient that the housing space S for housing the tank 72 is defined in the second housing 41, and for example, only the protruding housing 43 may be configured as a housing case.

In each of the above embodiments, the shape of the tank 72 is not limited to the example of each of the above embodiments. For example, the shape may be a cylindrical shape or a polygonal shape.

In each of the above embodiments, the heater 71 functions as the humidification promoting mechanism, however, an ultrasonic generator may be provided as a humidification promoting mechanism instead of the heater 71. In this case, the ultrasonic generator does not necessarily have to be in contact with the tank 72, and when the ultrasonic generator is installed such that a distance from the ultrasonic generator to water in the tank 72 is a desired value, the water in the tank 72 can be efficiently atomized by ultrasonic waves, and vaporization can be promoted.

In each of the above embodiments, the position of the attachment/detachment port 43K need not be on the upper side in the height direction Td of the second housing 41. For example, the attachment/detachment port 43K may open in the wall portion on the first end side in the length direction Ld of the second housing 41. In this case, a taking in/out direction of the tank 72 is the length direction Ld, and a bottom of the tank 72 is, of a wall portion of the tank 72, the wall portion on the second end side in the length direction Ld, which is on a side opposite to the attachment/detachment port 43K in the taking in/out direction of the tank 72.

In each of the above embodiments, the configuration is adopted in which air is supplied from the third introduction hole 48, and the air is discharged from the lid hole 50A of the tank 72, however, the direction in which the air flows is not limited to the example of each of the above embodiments. That is, air may be supplied from the third lead-out portion 50 to the tank 72, and pass through inside the tank 72, and the air may be discharged to the third introduction hole 48, via the first seal member 75. In this case, for example, it is sufficient that a unit that is not provided with the blower 31, but is provided with another blower is mounted to the third lead-out portion 50, and the blower is driven.

In each of the above embodiments, the first seal member need not extend in an annular shape so as to surround an entire periphery of the tank 72, when viewed from the taking in/out direction of the tank 72. It is sufficient that the first seal member 75 at least sandwiches the tank 72 from both sides in the length direction Ld, which is one direction orthogonal to the taking in/out direction. For example, in the first embodiment, the first seal member 75 may extend so as to surround, of side surfaces of the tank 72, the side surface on the second end side in the length direction Ld and the side surfaces on both the sides in the width direction Wd, and so as not to surround the side surface on the first end side in the length direction Ld. In this case, with the width direction Wd as the one direction, the tank 72 is sandwiched from both sides in the one direction.

In each of the above embodiments, the shape of the first seal member need not be a hollow member. In this case, for example, in the first embodiment, only a part that causes the first through-hole 76 and the second through-hole 77 to communicate with each other may be a space configuring the first downstream side flow path 54A, and the other parts may be solid members.

Figure 13:
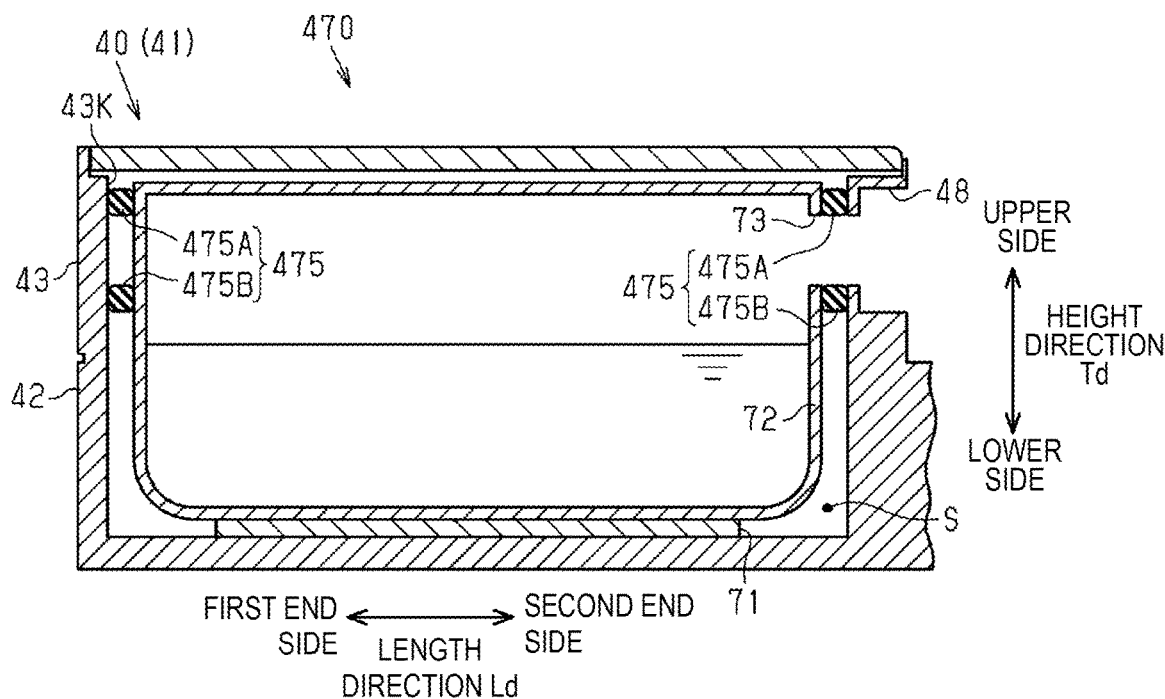
FIG. 13 is an end view of a base unit in a modification.

In each of the above embodiments, the first seal member is configured as a single member, but the first seal member may be configured with a plurality of members. In this case, for example, as illustrated in FIG. 13, in a humidifier 470, it is sufficient that a first seal member 475 is configured with an attachment/detachment port side seal member 475A, and a bottom surface side seal member 475B. The attachment/detachment port side seal member 475A is a solid member in an annular shape, and extends so as to surround an entire periphery of the tank 72, when viewed from a taking in/out direction of the tank 72. Then, the attachment/detachment port side seal member 475A is arranged closer to a side of the attachment/detachment port 43K than the first tank hole 73 and the third introduction hole 48 in the taking in/out direction of the tank 72. Further, the bottom surface side seal member 475B is a solid member in an annular shape, and extends so as to surround an entire periphery of the tank 72, when viewed from the taking in/out direction of the tank 72. Then, the bottom surface side seal member 475B is arranged closer to a bottom surface side of the tank 72 than the first tank hole 73 and the third introduction hole 48 in the taking in/out direction of the tank 72. According to such a configuration, the first seal member can be configured with two annular rings each having a relatively simple shape. Thus, advantage in terms of cost may be obtained.

In each of the above embodiments, the material for the first seal member is not limited to the example of each of the above embodiments. For example, the material for the first seal member may be resin or elastomer. When the material for the first seal member is elastomer, similarly to rubber, the first seal member has both ease of deformation and appropriate rigidity, thus, it is possible to achieve ease of insertion into the housing space S when the tank 72 is housed, and reliable positioning of the tank 72 in the second housing 41 in a compatible manner.

In each of the above embodiments, the configuration of the first fitting portion 43H and the second fitting portion 78 is not limited to the example of each of the above embodiments. For example, the convex shape of the first fitting portion 43H and the concave shape of the second fitting portion 78 may be configured to be reversed, or the first fitting portion 43H may be provided on the outer surface of the tank 72. Further, the first fitting portion 43H and the second fitting portion 78 need not be provided.

In the third embodiment, the shape of the in-tank flow path portion 281 is not limited to the example of the above third embodiment. For example, the opening of the in-tank flow path portion 281 on the inner side of the tank 72 may open to the second end side in the length direction Ld of the tank 72, or may be curved. The shape may be appropriately changed in accordance with the shape of the tank 72.

In the above first and third embodiments, the configuration of the lid 44 is not limited to the example of each of the above embodiments. For example, the lid 44 may be configured to rotate, with a side on the first end side in the length direction Ld as a rotation center.

Figure 14:
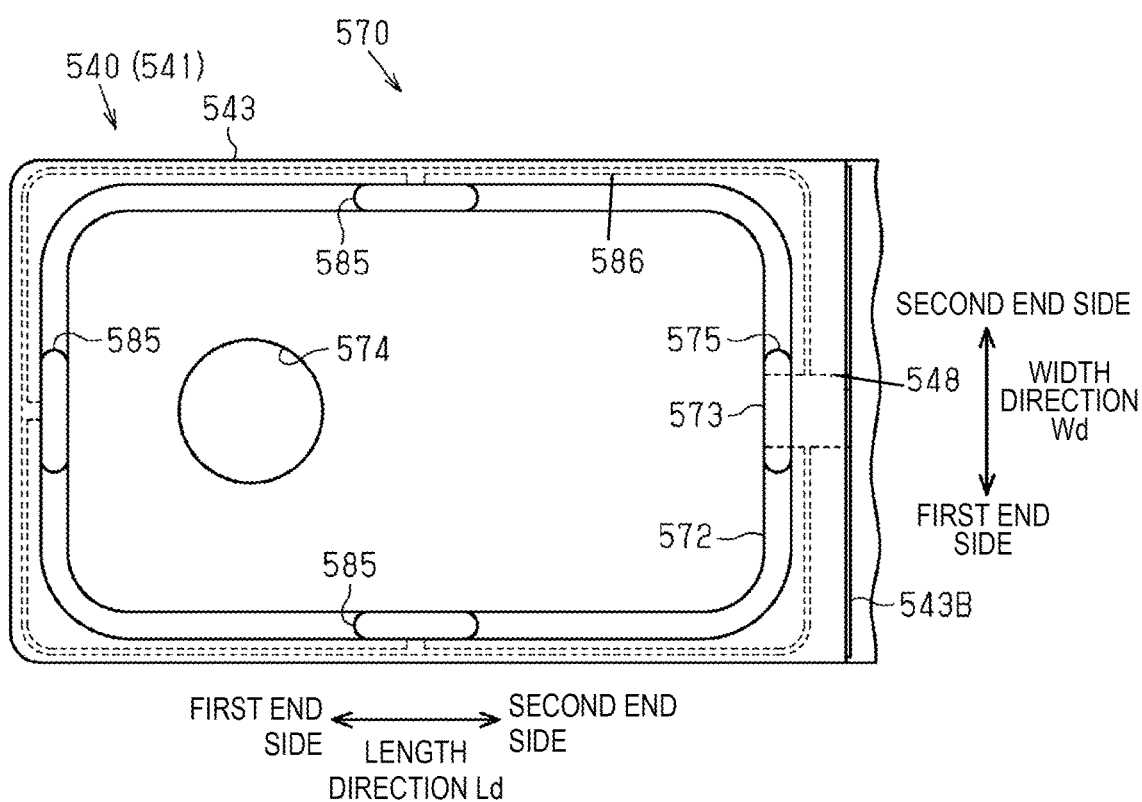
FIG. 14 is an end view of a base unit in a modification.

In each of the above embodiments, the tank 72 is sandwiched from both sides in one direction by the first seal member configured with a single member, however, the tank 72 may be sandwiched from both sides in one direction by the first seal member and another member. For example, as illustrated in FIG. 14, in a humidifier 570, a tank 572 may be sandwiched by a first seal member 575 and an elastic member 585 from both sides in one direction. To be specific, a third introduction hole 548 opens at a center in the width direction Wd of a second end surface 543B of a protruding housing 543 of a base unit 540.

A first tank hole 573 for supplying air to the tank 572 opens in a wall portion on a second end side in the length direction Ld of the tank 572. The first tank hole 573 causes the inside and the outside of the tank 572 to communicate with each other. A position of the first tank hole 573 coincides with a position of the third introduction hole 548, when viewed from the length direction Ld. The third introduction hole 548 causes the inside and the outside of the second housing 541 to communicate with each other. That is, in the present modification, the third introduction hole 548 functions as a first case hole. The first seal member 575 in an annular shape made of synthetic rubber is arranged between the tank 572 and the protruding housing 543. The first seal member 575 has a dimension that surrounds an opening edge of the third introduction hole 548 and the first tank hole 573, when viewed from the length direction Ld. Additionally, a second tank hole 574 for discharging air from the tank 572 opens in a wall portion on an upper side of the tank 572.

Here, in addition to the first seal member 575, three of the elastic members 585 are arranged between the tank 572 and the protruding housing 543. The elastic member 585 is a member in a hollow shape made of synthetic rubber, and the three elastic members 585 are positioned at both outer surfaces in the width direction Wd of the tank 572, and an outer surface on a first end side in the length direction Ld of the tank 572. In particular, the elastic member 585 positioned at the outer surface on the first end side in the length direction Ld of the tank 572 is arranged at the same position as that of the first seal member 575 in the width direction Wd. That is, the elastic member 585 positioned at the outer surface on the first end side in the length direction Ld of the tank 572 is arranged on a side opposite to the first seal member 575 with the tank 572 interposed therebetween in the length direction Ld which is one direction orthogonal to the taking in/out direction, when viewed from the taking in/out direction of the tank 572.

In addition, in this modification, an internal communication path 586 that causes a space inside the third introduction hole 548 and an internal space of each of the elastic members 585 to communicate with each other is defined inside the protruding housing 543. In a first use state, when air flows through the third introduction hole 548, the air flows into the elastic member 585 through the internal communication path 586. In this case, when trying to expand, the elastic member 585 can press the tank 572 to position the tank 572.

In each of the above embodiments, the humidifier 70 is not limited to be applied to the CPAP device 10. For example, the humidifier 70 may be applied to a respirator.

In each of the above embodiments, the configuration of the base unit 40 is not limited to the example of each of the above embodiments. For example, the second silencer 51 need not be provided.

In each of the above embodiments, the CPAP device 10 need not be used in the second use state. That is, the CPAP device 10 may be used only in the first use state, and used with the blower 31 constantly fixed to the base unit 40.

REFERENCE SIGNS LIST

10 CPAP DEVICE
20 MAIN BODY UNIT
21 FIRST HOUSING
21A FIRST END SURFACE
21B DENT PORTION
21C DENT SURFACE
21D LOWER SIDE SURFACE
21U UPPER SIDE SURFACE
22 OPERATION UNIT
22A SWITCH
22B SWITCH
23 FIRST INTRODUCTION PORT
24 FILTER
25 FIRST LEAD-OUT PORTION
27 FIRST CONNECTOR
31 BLOWER
32 MAIN FLOW PATH
33 FIRST SILENCER
34 PRESSURE SENSOR
35 FLOW RATE SENSOR
36 TEMPERATURE SENSOR
37 FIRST CONTROL UNIT
38 BATTERY
40 BASE UNIT
41 SECOND HOUSING
42 BASE HOUSING
42U UPPER SIDE SURFACE
43 PROTRUDING HOUSING
43B SECOND END SURFACE
43H FIRST FITTING PORTION
43K ATTACHMENT/DETACHMENT PORT
44 LID
45 PROTRUSION
46 SECOND INTRODUCTION PORT
47 SECOND LEAD-OUT PORT
48 THIRD INTRODUCTION HOLE
49 SECOND CONNECTOR
50 THIRD LEAD-OUT PORTION
50A LID HOLE
51 SECOND SILENCER
53 UPSTREAM SIDE FLOW PATH
54 DOWNSTREAM SIDE FLOW PATH
56 SECOND CONTROL UNIT
60 SEALING MEMBER
61 FIXING PORTION
62 PROTRUDING PORTION

70 HUMIDIFIER
71 HEATER
72 TANK
73 FIRST TANK HOLE
74 SECOND TANK HOLE
75 FIRST SEAL MEMBER
76 FIRST THROUGH-HOLE
77 SECOND THROUGH-HOLE
78 SECOND FITTING PORTION
79 SECOND SEAL MEMBER
80 HEATER TEMPERATURE SENSOR
91 AIR TUBE
92 MASK
93 USER
150 THIRD LEAD-OUT PORTION
170 HUMIDIFIER
172 TANK
172S CONTACT SURFACE
175 FIRST SEAL MEMBER
270 HUMIDIFIER
275 FIRST SEAL MEMBER
281 IN-TANK FLOW PATH PORTION
350 THIRD LEAD-OUT PORTION
370 HUMIDIFIER
374 SECOND TANK HOLE
375 FIRST SEAL MEMBER
382 EXHAUST SIDE CASE HOLE
383 THIRD THROUGH-HOLE
384 FOURTH THROUGH-HOLE
470 HUMIDIFIER
475 FIRST SEAL MEMBER
475A ATTACHMENT/DETACHMENT PORT SIDE SEAL MEMBER
475B BOTTOM SURFACE SIDE SEAL MEMBER
540 BASE UNIT
542 SECOND HOUSING
543 PROTRUDING HOUSING
543 SECOND END SURFACE
548 THIRD INTRODUCTION HOLE
570 HUMIDIFIER
572 TANK
573 FIRST TANK HOLE
574 SECOND TANK HOLE
575 FIRST SEAL MEMBER
585 ELASTIC MEMBER
586 INTERNAL COMMUNICATION PATH
901 O-RING
S HOUSING SPACE
US UPPER SIDE SPACE
LS LOWER SIDE SPACE

The invention claimed is:

1. A humidifier, comprising:
a housing case;
a water storage tank inside the housing case; and
a humidification promoting mechanism configured to vaporize water stored in the tank, wherein a gas humidified by the humidification promoting mechanism is discharged from the tank,
wherein an attachment/detachment port that enables the tank to be taken in and out opens in the housing case,
wherein a first case hole that communicates inside of the housing case with an outside of the housing case opens in the housing case,
wherein a first tank hole that communicates an inside of the tank with an outside of the tank opens in the tank,
wherein a first seal member separates a first gas flow path leading to an inside of the tank through the first case hole and the first tank hole from an external space of the housing case between the housing case and the tank, and
wherein the first seal member, when viewed in a direction perpendicular to a bottom surface of the tank, extends along an inner surface of the housing case, and sandwiches the tank from both sides in one direction parallel to the bottom surface of the tank.

2. The humidifier according to claim 1,
wherein the first seal member has a hollow shape, and
wherein the first seal member is provided with a communication hole that communicates an inside of the first seal member with the first gas flow path.

3. The humidifier according to claim 2,
wherein when a side of the attachment/detachment port in a taking in/out direction is defined as an upper side, and an internal space of the first seal member is divided into an upper side space that is closer to the attachment/detachment port than the first tank hole, and a lower side space that is closer to the bottom surface of the tank than the first tank hole,
a volume of the lower side space is larger than a volume of the upper side space.

4. The humidifier according to claim 1,
wherein the first seal member comprises rubber or elastomer.

5. The humidifier according to claim 1,
wherein the first seal member has an annular shape, when viewed from the direction perpendicular to the bottom surface of the tank.

6. The humidifier according to claim 1,
wherein an inner surface of the housing case or an outer surface of the tank is provided with a first fitting portion, and
wherein the first seal member is provided with a second fitting portion that is detachably fitted into the first fitting portion.

7. The humidifier according to claim 1,
wherein a contact surface in contact with the first seal member of an outer surface of the tank is inclined toward a direction in which the tank is taken in and out, and
wherein the contact surface faces an inside of the attachment/detachment port.

8. The humidifier according to claim 1,
wherein an in-tank flow path portion in a cylindrical shape extends from the first tank hole toward an inner side of the tank.

9. The humidifier according to claim 1, further comprising:
a lid configured to open and close the attachment/detachment port,
wherein a lid hole that communicates an inside of the housing case with an outside of the housing case opens in the lid,
wherein a second tank hole that communicates an inside of the tank with an outside of the tank opens in the tank and
wherein a second seal member is between the tank and the lid, the second seal member separates a second gas flow path leading to an inside of the tank through the lid hole and the second tank hole from an internal space of the housing case.

10. The humidifier according to claim 1,
wherein a second case hole that communicates an inside of the housing case with an outside of the housing case opens in the housing case, wherein a second tank hole that communicates an inside of the tank with an outside of the tank opens in the tank, and wherein the first seal member separates a second gas flow path leading to an inside of the tank through the second case hole and the second tank hole from an external space of the housing case.

11. The humidifier according to claim 1, wherein the first seal member comprises an attachment/detachment port side seal member in an annular shape, and a bottom surface side seal member in an annular shape, and wherein the attachment/detachment port side seal member is arranged closer to the attachment/detachment port than the first tank hole and the first case hole in a direction perpendicular to the bottom surface of the tank, and the bottom surface side seal member is arranged closer to the bottom surface of the tank than the first tank hole and the first case hole.

12. A humidifier, comprising:

a housing case;

a water storage tank inside the housing case; and a humidification promoting mechanism configured to vaporize water stored in the tank, wherein a gas humidified by the humidification promoting mechanism is discharged from the tank, wherein an attachment/detachment port that enables in and out the tank opens in the housing case, wherein a first case hole that communicates an inside of the housing case with an outside of the housing case opens in the housing case, wherein a tank hole that communicates an inside of the tank with an outside of the tank opens in the tank, wherein a first seal member separates a first gas flow path leading to an inside of the tank through the first case hole and the tank hole from an external space of the housing case between the housing case and the tank, wherein an elastic member is between the housing case and the tank, and wherein the elastic member, when viewed from a direction perpendicular to a bottom surface of the tank, is on a side opposite to the first seal member with the tank interposed therebetween, in one direction parallel to the bottom surface of the tank.

13. The humidifier according to claim 2, wherein the first seal member comprises rubber or elastomer.

14. The humidifier according to claim 3, wherein the first seal member comprises rubber or elastomer.

15. The humidifier according to claim 2, wherein the first seal member has an annular shape, when viewed from the direction perpendicular to the bottom surface of the tank.

16. The humidifier according to claim 3, wherein the first seal member has an annular shape, when viewed from the direction perpendicular to the bottom surface of the tank.

17. The humidifier according to claim 4, wherein the first seal member has an annular shape, when viewed from the direction perpendicular to the bottom surface of the tank.

18. The humidifier according to claim 2, wherein an inner surface of the housing case or an outer surface of the tank is provided with a first fitting portion, and wherein the first seal member is provided with a second fitting portion that is detachably fitted into the first fitting portion.

19. The humidifier according to claim 3, wherein an inner surface of the housing case or an outer surface of the tank is provided with a first fitting portion, and wherein the first seal member is provided with a second fitting portion that is detachably fitted into the first fitting portion.

20. The humidifier according to claim 4, wherein an inner surface of the housing case or an outer surface of the tank is provided with a first fitting portion, and wherein the first seal member is provided with a second fitting portion that is detachably fitted into the first fitting portion.

* * * * *